(12) United States Patent
Hager et al.

(10) Patent No.: US 9,283,675 B2
(45) Date of Patent: Mar. 15, 2016

(54) HUMAN-MACHINE COLLABORATIVE ROBOTIC SYSTEMS

(75) Inventors: Gregory Hager, Baltimore, MD (US); Nicolas Padoy, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 169 days.

(21) Appl. No.: 13/881,662

(22) PCT Filed: Nov. 14, 2011

(86) PCT No.: PCT/US2011/060638
§ 371 (c)(1),
(2), (4) Date: Apr. 25, 2013

(87) PCT Pub. No.: WO2012/065175
PCT Pub. Date: May 18, 2012

(65) Prior Publication Data
US 2013/0218340 A1    Aug. 22, 2013

Related U.S. Application Data

(60) Provisional application No. 61/412,587, filed on Nov. 11, 2010, provisional application No. 61/443,779, filed on Feb. 17, 2011.

(51) Int. Cl.
*B25J 9/16* (2006.01)
*A61B 19/00* (2006.01)
(Continued)

(52) U.S. Cl.
CPC ............ *B25J 9/163* (2013.01); *A61B 19/2203* (2013.01); *B25J 9/1671* (2013.01); *B25J 9/1689* (2013.01);
(Continued)

(58) Field of Classification Search
CPC ........... A61B 19/2203; A61B 19/5212; A61B 19/56; A61B 2019/223; A61B 2017/00207; A61B 2019/5265; A61B 2019/5255; B25J 9/1671; B25J 9/1697; G05B 2219/40099; G06F 3/017

USPC ................ 700/247, 250, 257, 258, 259, 264; 901/2, 3, 47; 1/247, 250, 257, 258, 1/259, 264
See application file for complete search history.

(56) References Cited

U.S. PATENT DOCUMENTS 8,068,095 B2 * 11/2011 Pryor ............................ 345/157
8,543,240 B2    9/2013 Itkowitz et al.
(Continued)

FOREIGN PATENT DOCUMENTS

CN           101870107 A   10/2010
WO   WO-2009/044287 A2    4/2009

OTHER PUBLICATIONS

Ahmadi et al., "Recovery of surgical workflow without explicit models," in International Conference on Medical Image Computing and Computer-Assisted Intervention (MICCAI), 2006, pp. 420-428.
(Continued)

*Primary Examiner* — Jason Holloway
(74) *Attorney, Agent, or Firm* — Venable LLP; Henry J. Daley; Laura G. Remus

(57) ABSTRACT

A semi-automatic, interactive robotic system for performing and/or simulating a multi-step task includes a user interface system, a recognition system adapted to communicate with the user interface system, a control system adapted to communicate with the recognition system, and a sensor-actuator system adapted to communicate with the control system. The recognition system is configured to recognize actions taken by a user while the user operates the user interface system and to selectively instruct the control system to cause the sensor-actuator system to perform, and/or simulate, one of an automatic step, a semi-automatic step or direct step of the multi-step task based on the recognized actions and a task model of the multi-step task.

18 Claims, 10 Drawing Sheets

(51) Int. Cl.
G09B 23/28 (2006.01)
G05B 19/427 (2006.01)
A61B 17/00 (2006.01)
(52) U.S. Cl.
CPC .............. *G05B 19/427* (2013.01); *G09B 23/28* (2013.01); *A61B 19/5212* (2013.01); *A61B 2017/00203* (2013.01); *A61B 2019/2223* (2013.01); *G05B 2219/35472* (2013.01); *G05B 2219/39004* (2013.01); *G05B 2219/39025* (2013.01); *G05B 2219/40116* (2013.01); *G05B 2219/40399* (2013.01); *G05B 2219/40413* (2013.01)

(56) References Cited

U.S. PATENT DOCUMENTS

| | | | |
|---|---|---|---|
| 8,880,223 B2* | 11/2014 | Raj et al. | 700/264 |
| 8,935,003 B2 | 1/2015 | Itkowitz et al. | |
| 2006/0166620 A1 | 7/2006 | Sorensen | |
| 2007/0142823 A1 | 6/2007 | Prisco et al. | |
| 2009/0062813 A1 | 3/2009 | Prisco et al. | |
| 2009/0157092 A1 | 6/2009 | Blumenkranz et al. | |
| 2009/0183125 A1* | 7/2009 | Magal et al. | 715/863 |
| 2010/0063630 A1* | 3/2010 | Sutherland et al. | 700/264 |
| 2010/0228249 A1* | 9/2010 | Mohr et al. | 606/41 |
| 2010/0234857 A1* | 9/2010 | Itkowitz et al. | 606/130 |
| 2010/0274087 A1 | 10/2010 | Diolaiti et al. | |
| 2011/0118748 A1 | 5/2011 | Itkowitz | |
| 2011/0288684 A1* | 11/2011 | Farlow et al. | 700/264 |
| 2012/0071891 A1 | 3/2012 | Itkowitz et al. | |
| 2012/0323364 A1* | 12/2012 | Birkenbach et al. | 700/257 |
| 2014/0018819 A1* | 1/2014 | Raj et al. | 606/130 |

OTHER PUBLICATIONS

Dam et al., "Quatemions, interpolation and animation," University of Copenhagen, Tech. Rep. DIKU-TR98/5, 1998.
Deguet et al., "The CISST libraries for computer assisted intervention systems," Insight Journal. [Online]. Available: http://hdl.handle.net/10380/1465a), 2008.
Guthart et al., "The intuitiveTM telesurgery system: Overview and application," in ICRA, 2000, pp. 618-621.
Kragic et al., Task modeling and specification for modular sensory based human-machine cooperative systems, in IROS, 2003, pp. 3192-3197.
Lin et al., Towards automatic skill evaluation: Detection and segmentation of robot-assisted surgical motions, Computer Aided Surgery, vol. 11, No. 5, pp. 220-230, 2006.
Lo et al., "Episode classification for the analysis of tissue/instrument interaction with multiple visual cues," in International Conference on Medical Image Computing and Computer-Assisted Intervention (MICCAI), 2003, pp. 230-237.
Markley et al., "Averaging quaternions," Journal of Guidance, Control, and Dynamics, vol, 30, No. 4, pp. 1193-1196, 2007.
Mayer et al., "A system for robotic heart surgery that learns to tie knots using recurrent neural networks," in IROS, 2006, pp. 543-548.
Nageotte et al., "Stitching planning in laparoscopic surgery: Towards robot-assisted suturing," Robotic Res., vol. 28, No. 10, pp. 1303-1321, 2009.
Padoy et al., "Workflow monitoring based on 3d motion features," in Proceedings of the International Conference on Computer Vision Workshops, IEEE Workshop on Video-oriented Object and Event Classification, 2009.
Rabiner, "A tutorial on hidden markov models and selected applications in speech recognition," Proceedings of the IEEE, vol. 77, No. 2, pp. 257-286, 1989.
Rosen et al., "Generalized approach for modeling minimally invasive surgery as a stochastic process using a discrete markov model," IEEE Trans, on Biomedical Engineering, vol. 53, No. 3, pp. 399-413, 2006.
Sakoe et al., "Dynamic programming algorithm optimization for spoken word recognition," IEEE Trans. Acoust. Speech Signal Process., vol. 26, No. 1, pp. 43-49, 1978.
Speidel et al., "Recognition of risk situations based on endoscopic instrument tracking and knowledge based situation modeling," in Med. Imaging. SPIE, 2008.
Staub et al., "Automation of tissue piercing using circular needles and vision guidance for computer aided laparoscopic surgery," in ICRA, 2010, pp. 4585-459.
van den Berg et al., "Superhuman performance of surgical tasks by robots using iterative learning from human-guided demonstrations," in ICRA, 2010, pp. 2074-2081.
Varadarajan et al., "Data-derived models for segmentation with application to surgical assessment and training," in MICCAI (1), 2009, pp. 426-434.
Wang et al., "Alignment of curves by dynamic time warping," Annals of Statistics, vol. 25, No. 3, pp. 1251-1276, 1997.
Yoshimitsu et al., "Development and evaluation of the second version of scrub nurse robot (snr) for endoscopic and laparoscopic surgery," in IROS, 2007, pp. 2288-2294.
Zhou et al., "Canonical time warping for alignment of human behavior," in Advances in Neural Information Processing Systems Conference (NIPS), Dec. 2009.
International Search Report and Written Opinion of PCT/US2011/060638.
Graves et al., "Action selection in teleautonmous systems," Proceedings of the 1995 IEEE/RSJ International Conference on Intelligent Robots and Systems, IROS 95, Human Robot Interaction and Cooperative Robots, 1995, pp. 14-19.
Sato et al., "Active understanding of human intention by a robot through monitoing of human behavior," Proceedings of the IEEE/RSJ/GI International Conference on Intellgent Robots and Systems:Advanced Robotics Systems and the Real World, 1994, vol. 1, pp. 405-414.
Yokokohji et al., "Operation modes for cooperating with autonomous functions in intelligent teleoperation systems," Proceedings of the International Conference on Robotics and Automation, 1993, vol. 10, pp. 510-515.
Demeester et al., "User-adapted plan recognition and use-adapted shared control" A Bayesian approach to semi-autonomous wheelchair driving, Autonomous Robots, 2007, vol. 24, pp. 193-211.
Padoy et al., "Human-Machine Collaborative Surgery Using Learned Models," 2011 IEEE International Conference on Robotics and Automation, May 9-13, 2011, pp. 5285-5292.
Padoy et al., "On-Line Recognition of Surgical Activity for Monitoring in the Operating Room," Proceedings of the 20th Conference on Innovative Applications of Artificial Intelligence, AAAI/IAAI 2008.
Padoy et al., "A Boosted Segmentation Method for Surgical Workflow Analysis," Proceedings of Medical Image Computing and Computer-Assisted Intervention, MICCAI 2007.
Reiley et al., "A Review of Methods for Objective Surgical Skill Evaluation," Surgical Endoscopy, 2010, vol. 25, pp. 356-366.
Reiley et al., "Motion generation of robotic surgical tasks: Learning from expert demonstrations," 32 Annual International Conference of the IEEE Engineering in Medicine and Biology Society (EMBC), 2010.

\* cited by examiner

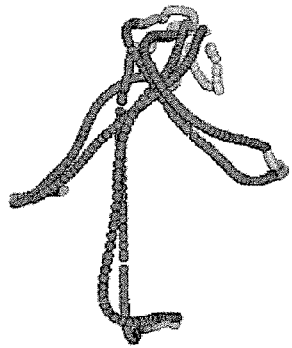
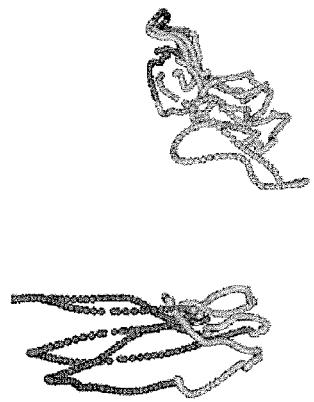
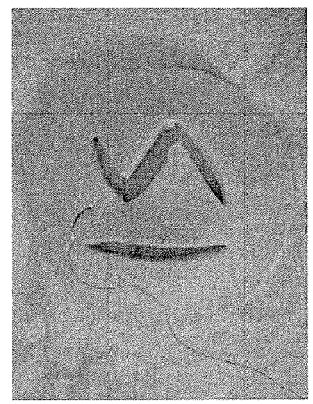
Figure 6(a)
Figure 6(b)
Figure 7(a)
Figure 7(b)

(a) Pin Task

HUMAN-MACHINE COLLABORATIVE ROBOTIC SYSTEMS

CROSS-REFERENCE OF RELATED APPLICATION

This application claims priority to U.S. Provisional Application No. 61/412,587 filed Nov. 11, 2010, and U.S. Provisional Application No. 61/443,779 filed Feb. 17, 2011, the entire contents of which are hereby incorporated by reference, and is a U.S. National Stage Application under 35 U.S.C. §371 of PCT/US2011/060638, filed Nov. 14, 2011, the entire contents of which are incorporated herein by reference.

This invention was made with U.S. Government support of Grant No. CPS 0931805, awarded by the NSF. The U.S. Government has certain rights in this invention.

BACKGROUND

1. Field of Invention

The field of the currently claimed embodiments of this invention relates to robotic systems and more particularly to semi-automatic, interactive robotic systems and simulated semi-automatic, interactive robotic systems.

2. Discussion of Related Art

Robotic systems can be useful for the performance of repetitive, complex, intricate and/or dangerous tasks. As applied to surgery, for example, complex procedures represent a high workload for the surgeon. In addition, the recent introduction of robots into the surgery room has led to the need for new techniques to train and evaluate surgeons. For this reason, surgical gesture modeling has attracted significant attention in recent years, and several methods, usually using Hidden Markov Models or variations thereof, have been proposed for off-line skill modeling and classification (J. Rosen, J. Brown, L. Chang, M. Sinanan, and B. Hannaford, "Generalized approach for modeling minimally invasive surgery as a stochastic process using a discrete markov model," IEEE Trans, on Biomedical Engineering, vol. 53, no. 3, pp. 399-413, 2006; H. C. Lin, I. Shafran, D. Yuh, and G. D. Hager, "Towards automatic skill evaluation: Detection and segmentation of robot-assisted surgical motions," Computer Aided Surgery, vol. 11, no. 5, pp. 220-230, 2006; B. Varadarajan, C. E. Reiley, H. Lin, S. Khudanpur, and G. D. Hager, "Data-derived models for segmentation with application to surgical assessment and training," in MICCAI (1), 2009, pp. 426-434).

With the development of dexterous robots, different groups have proposed techniques to automate specific surgical tasks. An example of a task that has been addressed is knot tying. In (H. G. Mayer, F. J. Gomez, D. Wierstra, I. Nagy, A. Knoll, and J. Schmidhuber, "A system for robotic heart surgery that learns to tie knots using recurrent neural networks," in IROS, 2006, pp. 543-548), recurrent neural networks are used to learn a loop trajectory from demonstration. In (J. van den Berg, S. Miller, D. Duckworth, H. Hu, A. Wan, X.-Y. Fu, K. Goldberg, and P. Abbeel, "Superhuman performance of surgical tasks by robots using iterative learning from human-guided demonstrations," in ICRA, 2010, pp. 2074-2081), robot dynamics are learned to replay the trajectory at an increased speed. The needle insertion task has also attracted much attention: a geometric task model is designed in (F. Nageotte, P. Zanne, C. Doignon, and M. de Mathelin, "Stitching planning in laparoscopic surgery: Towards robot-assisted suturing," Robotic Res., vol. 28, no. 10, pp. 1303-1321, 2009) to compute the path-planning of the needle insertion. In (C. Staub, T. Osa, A. Knoll, and R. Bauernschmitt, "Automation of tissue piercing using circular needles and vision guidance for computer aided laparoscopic surgery," in ICRA, 2010, pp. 4585-4590), a circular motion is automated for needle insertion after the surgeon has marked the insertion point with a laser-pointer. There remains, however, a need for automation methods that either deal with the environment such as tissues and suture threads or that provides collaboration with the operator.

A natural way to allow for collaboration between a robot and the operator is to change the interaction mode based on the current context. This has been demonstrated on a curve following task in microsurgery by using virtual fixtures to impose path constraints on the manipulator (D. Kragic and G. Hager, "Task modeling and specification for modular sensory based human-machine cooperative systems," in IROS, 2003, pp. 3192-3197).

Context modeling for real-time recognition of the current surgical task has been addressed in

- B. P. L. Lo, A. Darzi, and G.-Z. Yang, "Episode classification for the analysis of tissue/instrument interaction with multiple visual cues," in International Conference on Medical Image Computing and Computer-Assisted Intervention (MICCAI), 2003, pp. 230-237.
- K. Yoshimitsu, F. Miyawaki, T. Sadahiro, K. Ohnuma, Y. Fukui, D. Hashimoto, and K. Masamune, "Development and evaluation of the second version of scrub nurse robot (snr) for endoscopic and laparoscopic surgery," in IROS, 2007, pp. 2288-2294.
- S. Speidel, G. Sudra, J. Senemaud, M. Drentschew, B. P. Mller-Stich, C. Gutt, and R. Dillmann, "Recognition of risk situations based on endoscopic instrument tracking and knowledge based situation modeling," in Med. Imaging. SPIE, 2008.
- N. Padoy, D. Mateus, D. Weinland, M.-O. Berger, and N. Navab, "Workflow monitoring based on 3d motion features," in Proceedings of the International Conference on Computer Vision Workshops, IEEE Workshop on Video-oriented Object and Event Classification, 2009.

typically using automata or Hidden Markov Models. However, these approaches do not allow for human-machine interactions to perform the operation. There thus remains a need for improved human-machine collaborative robotic systems.

SUMMARY

A semi-automatic, interactive robotic system for performing a multi-step task according to some embodiments of the current invention includes a user interface system, a recognition system adapted to communicate with the user interface system, a control system adapted to communicate with the recognition system, and a sensor-actuator system adapted to communicate with the control system. The recognition system is configured to recognize actions taken by a user while the user operates the user interface system and to selectively instruct the control system to cause the sensor-actuator system to perform one of an automatic step, a semi-automatic step or direct step of the multi-step task based on the recognized actions and a task model of the multi-step task.

A semi-automatic, interactive robotic simulation system for simulating a multi-step task according to some embodiments of the current invention includes a user interface system, a recognition system adapted to communicate with the user interface system, a control system adapted to communicate with the recognition system, and a simulated sensor-actuator system adapted to communicate with the control system. The recognition system is configured to recognize actions taken by a user while the user operates the user interface system and to selectively instruct the control system to cause the simulated sensor-actuator system to simulate the performance of one of an automatic step, a semi-automatic step or direct step of the multi-step task based on the recognized actions and a task model of the multi-step task.

BRIEF DESCRIPTION OF THE DRAWINGS

Further objectives and advantages will become apparent from a consideration of the description, drawings, and examples.

FIGS. 6(a) and 6(b) show a Pin Task performed with a single instrument according to an embodiment of the current invention. FIG. 6(a) shows the start & end state of the pod. FIG. 6(b) shows example trajectories of the instrument. The red (dark) parts indicate the segments annotated for automation.

FIGS. 7(a) and 7(b) show a Suturing Task performed with two instruments. FIG. 7(a) shows start & end state of the pod. FIG. 7(b) shows example trajectories of the two instruments. They normally intersect, but have been isolated for better visualization. The red (dark) parts indicate the segments annotated for automation.

FIG. 9(a) shows input trajectories (dotted lines) and average trajectory (black continuous line). FIG. 9(b) shows input trajectories (continuous lines) and average trajectory (black dotted line). Emphasis on rotational motion, illustrated by displaying one frame axis over time.

FIG. 10(a) shows a Pin Task: 3D motion of the master manipulator. Manual performance (left) versus HMC performance (right) displayed side-to-side using the same scale. FIG. 10(b) shows a Suturing Task: 3D motions of the left and right master manipulators. Manual (left) versus HMC (right) performance displayed side-to-side using the same scale. The left ellipse always corresponds to the left manipulator.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

According to some embodiments of the current invention, tele-operated robotic assistants can offer the possibility of performing certain commonly occurring tasks autonomously. Some embodiments of the current invention can provide a novel surgical Human-Machine Collaborative (HMC) system by using a natural division of tasks into subtasks, also called "steps", in which portions of a surgical task are performed autonomously under complete surgeon's control while other portions are performed manually. A robotic system according to an embodiment of the current invention automatically identifies the completion of a manual subtask (step), seamlessly executes the next automated task or step, and then returns control back to the surgeon. An embodiment of the current invention is based on learning from demonstration. This embodiment uses Hidden Markov Models for the recognition of task completion and temporal curve averaging for learning the executed motions. For some examples, a da Vinci tele-surgical robot is modified according to an embodiment of the current invention. We show on two illustrative tasks where such human-machine collaboration is intuitive and that automated control improves the usage of the master manipulator workspace. Because such a system does not limit the traditional use of the robot, but enhances its capabilities while leaving full control to the surgeon, it provides a safe and acceptable solution for surgical performance enhancement.

Although some embodiments and examples of the current invention described in detail below are directed to surgical robots, the general concepts of the current invention are not limited to only surgical robots. Other embodiments of the current invention include other types of robotic systems, such as, but not limited to, manufacturing and/or assembly robots, and remotely operated robots for use in dangerous or remote environments, for example.

As used herein, the term "task" is intended to generally include any multi-step process to be performed by a robotic system. For example, in the case of a surgical robot, a task can be at least a portion of a surgical procedure. The term "step" is intended to include at least one translation and/or rotation of at least a portion of the actuator assembly.

Figure 1:
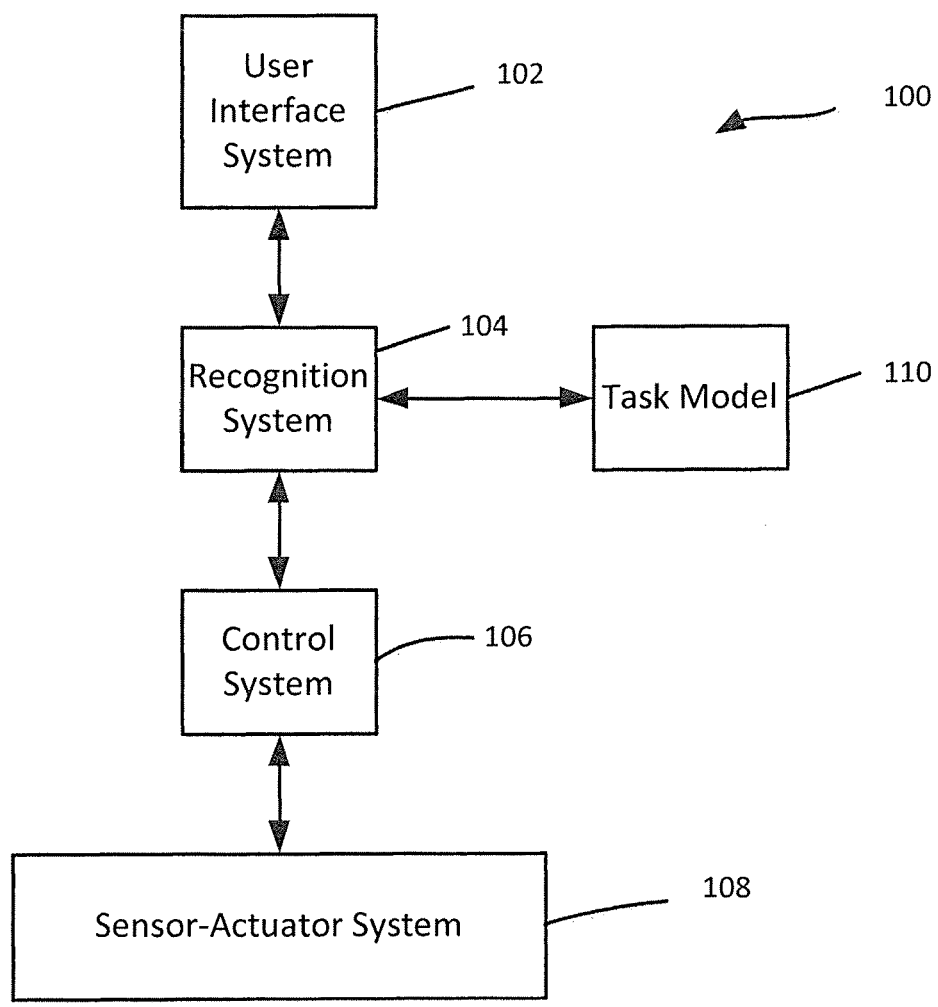
FIG. 1 is a schematic illustration of a semi-automatic, interactive robotic system for performing a multi-step task according to an embodiment of the current invention.

FIG. 1 provides a schematic illustration of a semi-automatic, interactive robotic system 100 for performing a multi-step task according to an embodiment of the current invention. The semi-automatic, interactive robotic system 100 includes a user interface system 102, a recognition system 104 adapted to communicate with the user interface system 102, a control system 106 adapted to communicate with the recognition system 104, and a sensor-actuator system 108 adapted to communicate with the control system 106. The recognition system 104 is configured to recognize actions taken by a user while the user operates the user interface system 102 and to selectively instruct the control system 106 to cause the sensor-actuator system 108 to perform one of an automatic step, a semi-automatic step or direct step of the multi-step task based on the recognized actions and a task model 110 of the multi-step task.

The user interface system 102 can include controls to be operated by one, two, or more operators. The controls can be hand-operated controls, but can alternatively, or in addition, include controls that can be operated by other parts of the user's body, such as, but not limited to, foot pedals. For example, conventional surgical robots include a clutch pedal to allow the user to disengage one or more sensor-actuator components from control by the robot. This can be useful for crude adjustments and/or emergency disengagement, for example. The user interface system 102 can also include observation and/or display systems so that the one or more users can observe the patient being operated on, or the product being assembled, for example. In some embodiments, the display system can display images, such as, but not limited to medical images. For example, in the case of surgical applications, the images could include, but are not limited to, real-time optical images, real-time ultrasound, real time OCT images and/or other modalities, or could include preoperative images, such as MRI, CT, PET, etc. The various image modalities can be selectable, programmed, superimposed and/or can include other information superimposed in graphical and/or numerical or symbolic form, for example.

The recognition system 104 can be implemented on a computer or any other suitable data processing and storage devices, for example. In some embodiments, the recognition system 104 can comprise computer-executable instructions stored on a computer that perform the recognition and other processes. However, in alternative embodiments, the recognition system can be a hard-wired device rather than software instructions stored on a computer. The computer can be a local computer, such as a work station, a desk-top, or a lap-top computer, for example, or could be a remotely located and/or a distributed computer system connected through a network, for example. The computer can also include one or more data storage and memory devices. The task model 110 can be stored on a data storage device of the computer, for example. The recognition system can use the kinematics of the robot in order to recognize particular motions of the user in some embodiments. Based on a task model, such motion can be identified with a step in performing a multi-function task. Alternatively, or in addition, the user interface system 102 and/or the sensor-actuator system 108 can include an observation system to more directly observe motions of the user, or users, and/or motion of components of the sensor-actuator system and/or patients or objects being manipulated. An observation system could include, but is not limited to, one or more camera to be able to observe and segment moving objects, for example.

The recognition system 104 can operate analogous to a switching system in the sense that it determines whether an automatic step, a semi-automatic step or a direct step is to be performed by the sensor-actuator system under the control of the control system. A direct step can be a step that is performed similar to, or the same as, a step would be performed under a conventional tele-operated robotic system. An automatic step can be a step carried out completely under the control of the robot. For example, the user may move at least a portion of the sensor actuator system to a location in which further steps are to be performed. This first motion is one possible example of a direct step. The recognition system may then recognize this step was taken by the user and, based on a task model, instruct the performance of an automatic step. For example, the recognition system could provide instructions for the portion of the sensor-actuator system that was moved in a direct step to move to a location to pick up and return with an object, such as, but not limited to, a surgical tool or suture for a surgical procedure, or an assembly tool or assembly piece for an assembly operation. This is just one illustrative example, and not intended to limit the scope of the current invention. One should recognize that there are an extremely large number of possible examples.

In another example, the recognition system 104 may recognize that the user moved a portion of the sensor-actuator system into position to perform a step of a multi-step task and the recognition system, based on the task model, provides instructions for another portion of the sensor-actuator system to perform another step to assist the user. One example, without limitation, is for the user to operate one robotic arm while the recognition system instructs the operation of another robotic arm to assist the user. An automatic step could be holding an object for the user, for example. In a surgical procedure, this could be holding a light, a camera, an endoscope, or holding suture to be snipped, for example. In an assembly operation, this could be holding and/or manipulating a product being assembled so that the user can attach a part, for example. These examples are given to help explain some concepts of the current invention and are not intended to limit the scope. It should be clear to one of ordinary skill in the art that a very large number of such examples are possible within the broad concepts of the current invention.

In some embodiments, the user input system can include an input device adapted to permit the user to at least one of manually or verbally input commands to be communicated to the recognition system to at least one of initiate or modify instructions to be provided to the control system. This can include, but is not limited to, hand signals provided by the user while and/or separate from manipulating the controls for the sensor-actuator system.

Figure 2:
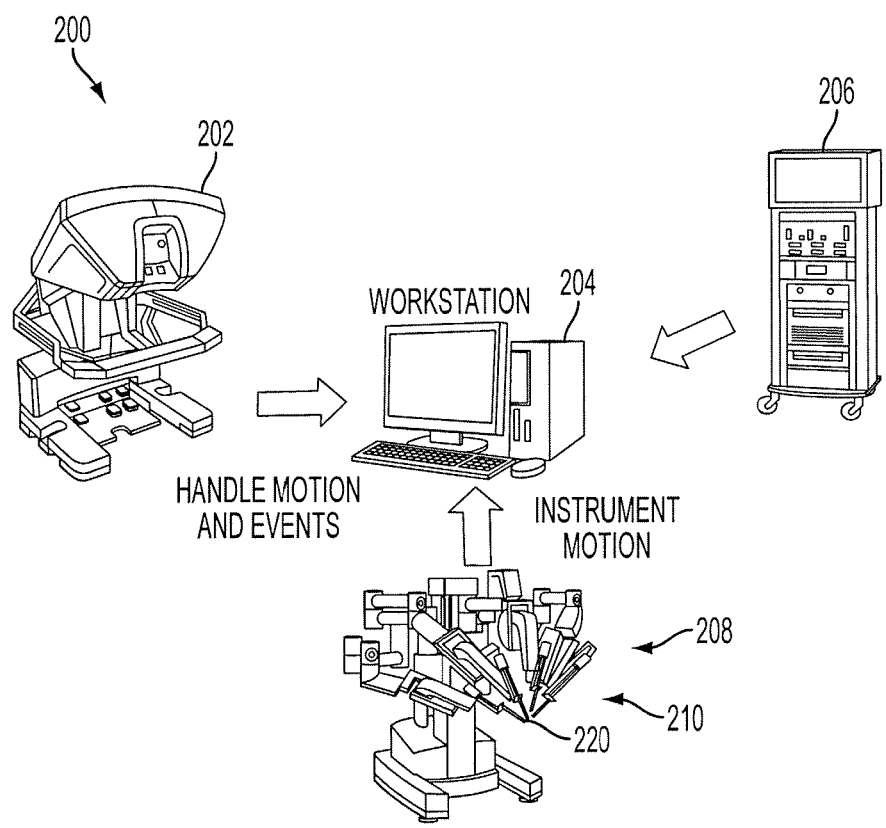
FIG. 2 is an illustration of a semi-automatic, interactive robotic system for performing a multi-step task according to another embodiment of the current invention.
Figure 3:
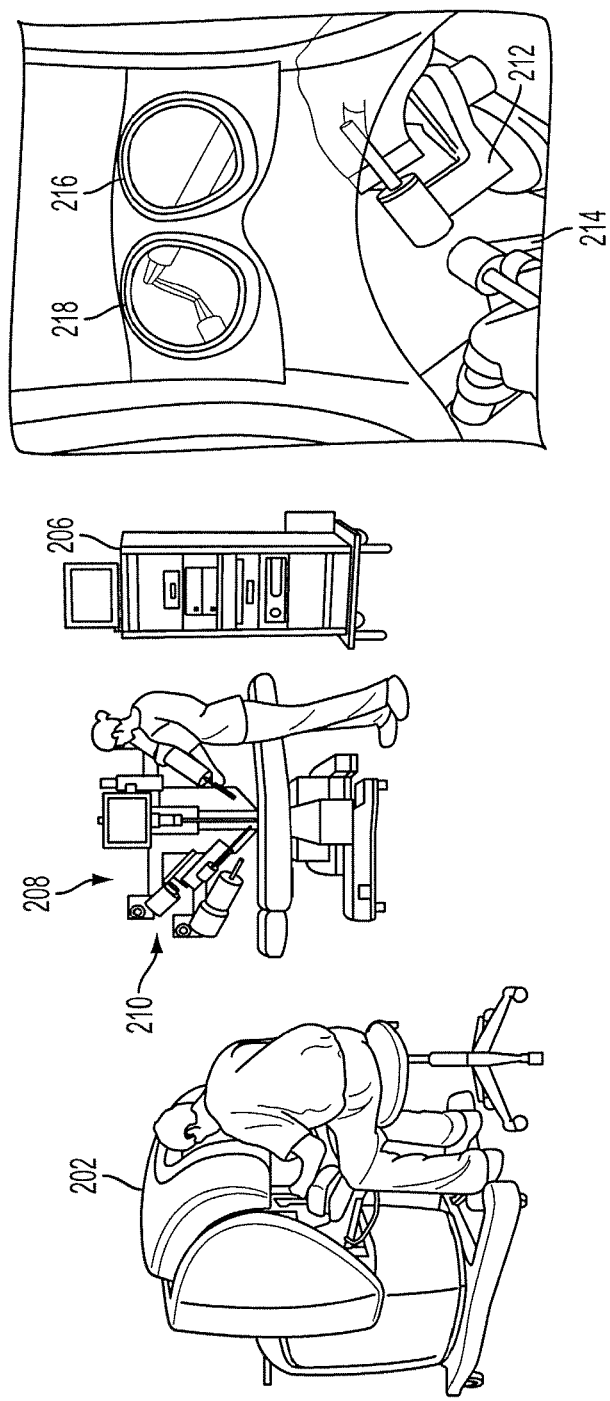
FIG. 3 is another view of the semi-automatic, interactive robotic system shown in FIG. 2.

FIGS. 2 and 3 illustrate a semi-automatic, interactive robotic system 200 according to an embodiment of the current invention. In this example, the semi-automatic, interactive robotic system 200 is a surgical robotic system, such as a modified DA VINCI robotic system. In this example, the user interface system 202 is a surgeon console. The workstation 204 and/or data processing and storage system 206 is configured to include the recognition system and the task model. The sensor-actuator system 208 is a surgical robotic sensor-actuator system that includes a plurality of articulated arms 210. The control system can be included in the workstation 204, the data processing and storage system 206 and/or the sensor-actuator system 208. The user interface system 202 includes right hand 212 and left hand 214 controls and right eye 216 and left eye 218 displays. At least one of the plurality of articulated arms 210 can include at least one of a gripper or a tool attachment assembly 220.

In some embodiments of the current invention, the task model can be a Hidden Markov Model, for example. However, the broad concepts of the current invention are not limited to only Hidden Markov Models. For example, other models which do not require the Markov property to be a good approximation could also be used in other embodiments of the current invention. In some embodiments of the current invention, the task model can be a machine-learning model.

In other embodiments of the current invention, the sensor-actuator system 108 and/or 208 can be simulated rather being an actual physical system. This can be useful for simulating tasks performed by the semi-automatic, interactive robotic system 100 and/or 200. Simulations can be useful for training users, for example. However, they could also be useful for other purposes, such as, but not limited to planning a task to be performed and/or conducting experiments or tests of various possible tasks.

The following specific examples are presented to help explain some concepts of the current invention in more detail. However, the broad concepts of the current invention are not intended to be limited to the specific examples.

EXAMPLES

The increased use of tele-surgical robots, such as the DA VINCI surgical system from INTUITIVE SURGICAL, Inc., provides new ways to teach, assess and perform surgeries. On the one hand, large sets of objective performance data can be collected from the robots (H. C. Lin, I. Shafran, D. Yuh, and G. D. Hager, "Towards automatic skill evaluation: Detection and segmentation of robot-assisted surgical motions," Computer Aided Surgery, vol. 11, no. 5, pp. 220-230, 2006). On the other hand, the technology can permit automation of specific surgical tasks in the near future (J. van den Berg, S. Miller, D. Duckworth, H. Hu, A. Wan, X.-Y. Fu, K. Goldberg, and P. Abbeel, "Superhuman performance of surgical tasks by robots using iterative learning from human-guided demonstrations," in ICRA, 2010, pp. 2074-2081). However, it has been unclear how collected performance data can be used to design efficient human-machine collaborative systems that can adapt to the operator, to the surgical environment, and also provide seamless assistance during the surgery.

In this example, we show a Human-Machine Collaborative (HMC) system that learns, from surgical demonstration, how to collaboratively assist the surgeon during a tele-operated task according to an embodiment of the current invention. This is complementary to previous work focusing on pure automation (H. G. Mayer, F. J. Gomez, D. Wierstra, I. Nagy, A. Knoll, and J. Schmidhuber, "A system for robotic heart surgery that learns to tie knots using recurrent neural networks," in IROS, 2006, pp. 543-548; F. Nageotte, P. Zanne, C. Doignon, and M. de Mathelin, "Stitching planning in laparoscopic surgery: Towards robot-assisted suturing," Robotic Res., vol. 28, no. 10, pp. 1303-1321, 2009; Berg10). Here, the task is broken down into manual and potentially automatable subtasks. The system then assists the operator by recognizing, in real-time, the completion of manual subtasks and automates the remaining ones. It also provides contextual Augmented Reality (AR) information in the operator's view to reduce his/her cognitive workload. The subtasks to be automated were chosen so as to permit an optimized usage of the operator workspace. They involve transport tasks having no interaction with the environment. During tele-operation, transitions between manual and automated execution are automatic and seamless. Moreover, the operator has the possibility of intervening during the automatic execution to correct the trajectory if needed.

Figure 4:
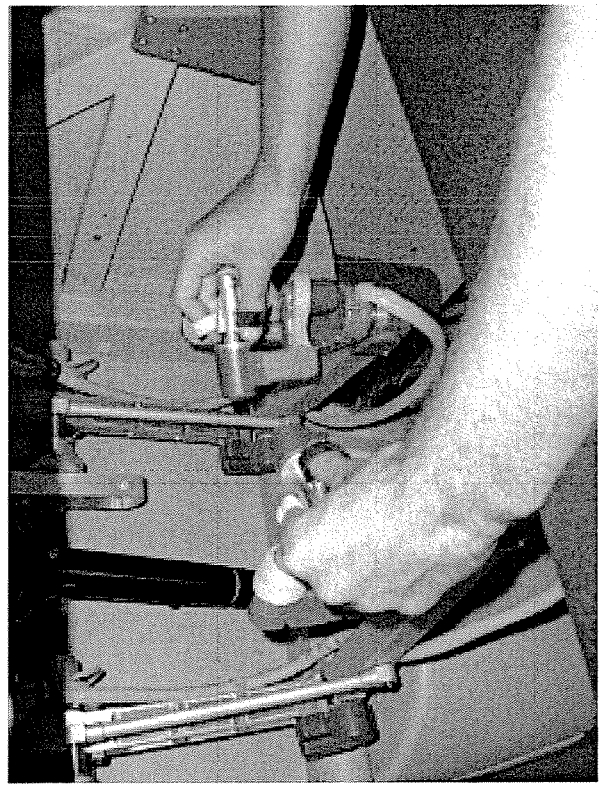
FIG. 4 shows an example of a configuration of the da Vinci robot adapted for use according to an embodiment of the current invention. Patient side manipulators plus endoscopic camera (left) and master manipulators (right) are shown.
Figure 4:
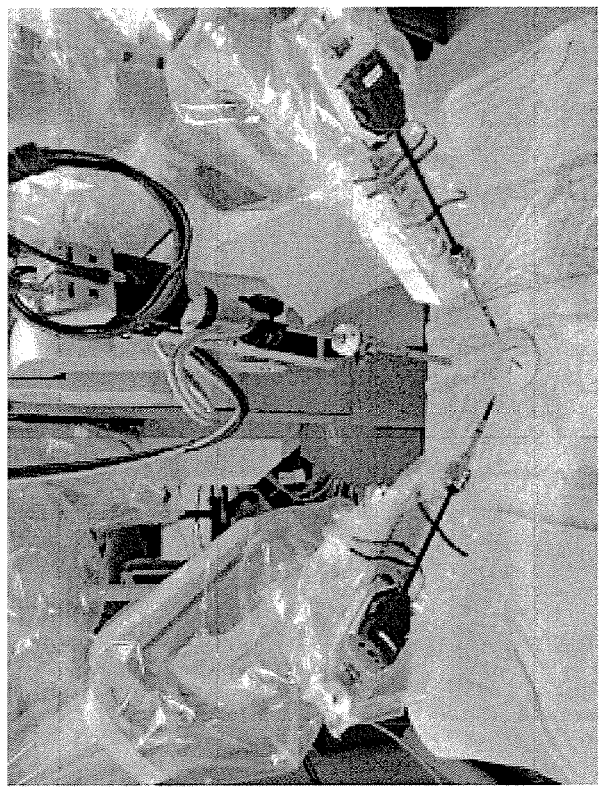

We validate our approach using a DA VINCI surgical robot (G. Guthart and J. K. S. Jr., "The Intuitive™ telesurgery system: Overview and application," in ICRA, 2000, pp. 618-621) used exclusively for research purposes. The robot consists of two master console manipulators that tele-operate three patient-side manipulators under stereo endoscopic visualization (see FIG. 4). We first record kinematic data from the robot while an operator performs the task a few times and annotates segments of the data corresponding to subtasks that should be automated. We then use an approach based on Hidden Markov Models (HMMs) to determine, in real-time, the completion of the current manual subtask. Once the transition to automatic execution is activated, the instrument motion corresponding to the automatic subtask is provided to the robot. This motion is learned from the demonstration data using a temporal curve averaging approach based on Dynamic Time Warping (DTW). Finally, for supervision purposes, we display an overlay of the planned trajectory in the stereo view of the operator.

We use two manipulative tasks to demonstrate our approach: moving three pins to the cardinal locations of a training pod and performing a running suture on a suturing pod. Our experiments show that such a Human-Machine Collaborative framework is intuitive and can highly improve the usage of the operator's workspace, by reducing large movements from the master manipulators and thereby the need for clutching to readjust the hand positions.

Task Model

For the purposes of this example, we consider a task to consist of an ordered set of subtasks (or steps) that need to be executed in a sequential temporal order. To ease the presentation, we assume that the tasks alternate between a manual and an automated subtask, starting with a manual subtask. This can be achieved by aggregating the consecutive subtasks of each type—manual or automated—as a single atomic subtask.

Let a task $\mathcal{T}$ consist of a sequence of subtasks $\mathcal{T}_1, \ldots, \mathcal{T}_N$, where N=2n. $\mathcal{T}_2, \mathcal{T}_4, \ldots, \mathcal{T}_N$ are assumed to be the automated subtasks. In this example, such subtasks are the ones which do not involve interactions with the environment or fine manipulations, but require larger motions instead.

Figure 5:
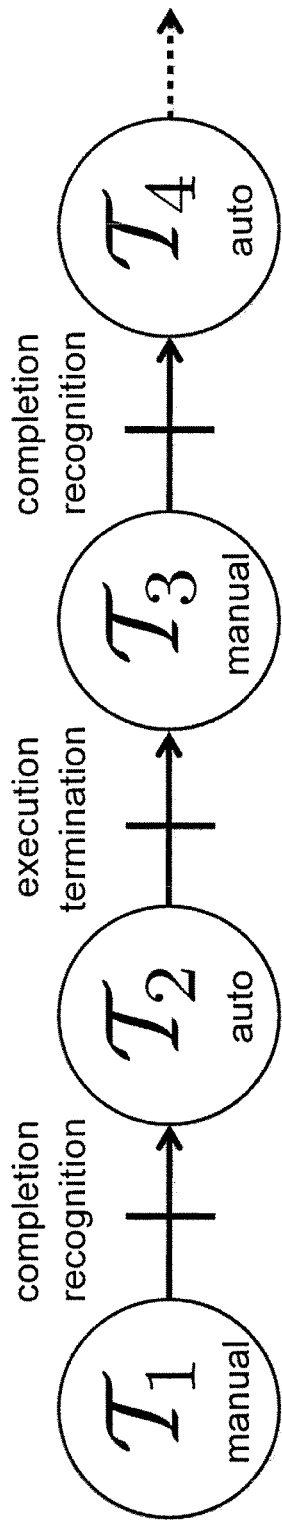
FIG. 5 is a schematic illustration of a task model according to an embodiment of the current invention, including transitions between manual and automatic subtasks.

FIG. 5 briefly illustrates the task model, which can be seen as an automata in which transitions are either triggered by the recognition of the manual subtask completion or by the termination of the automatic subtask.

Illustrative Tasks

The two tasks used to demonstrate our approach are illustrated in FIGS. 6 and 7. The first task, called pin-task, requires a single instrument and consists in displacing three pins to three cardinal locations (FIG. 6(a)). The task consists of six large transportation motions learned by the system and of six fine motions executed by the operator, consisting in grasping and pinning. A summary of the subtasks is shown in Table 1. The motion performed by the instrument is displayed on FIG. 6(b), in which the transportation and fine motions are represented with different colors.

TABLE 1

Pin Task description.

| # | Name |
|---|------|
| 1 | Grab pin1 from East |
| 2* | Move pin1 to North |
| 3 | Pin pin1 |
| 4* | Move tool back to East |
| 5 | Grab pin2 |
| 6* | Move pin2 to West |
| 7 | Pin pin2 |
| 8* | Move tool back to East |
| 9 | Grab pin3 |
| 10* | Move pin3 to South |
| 11 | Pin pin3 |
| 12* | Move tool back to East |

The star (*) indicates the automated subtasks.

The second task, called sut-task, requires two instruments (referred to by left and right) and consists of performing a running suture with three needle insertions (FIG. 7(a)). It consists of five generic motions repeated at three successive locations. Three fine motions are performed by the surgeon: grasping needle with right instrument, inserting needle and grasping needle with left instrument. Two transportation motions are learned and automated: pulling thread out with left instrument and handing in the needle back to the right instrument at the location of the next suture point. All the subtasks, concatenated into manual/automated subtasks, are listed in Table 2. The motions performed by the two instruments are displayed on FIG. 7(b), in which the transportation and fine motions are represented with different colors.

TABLE 2

Suturing Task description.

| # | Name |
|---|------|
| 1 | Grasp needle (RT) from pod, move to 1st suture point (RT), Insert needle (RT), grasp it (LT) |
| 2* | Pull thread out (LT), move back to 2nd suture point (LT) |
| 3 | Grasp needle (RT) from (LT), Insert needle (RT), grasp it (LT) |
| 4* | Pull thread out (LT), move back to 3rd suture point (LT) |
| 5 | Grasp needle (RT) from (LT) Insert needle (RT), grasp it (LT) |
| 6* | Pull thread out (LT), move back to pod end point (LT) |

*indicates automated subtasks.
(RT) stands for "Right Tool" and (LT) for "Left Tool".

Robotic Environment

In our setup, the pod used to accomplish the task can be manipulated by two patient side manipulators (PSMs) having each 7 degrees of freedom (DOFs). Each PSM controls a surgical instrument. In our case the PSMs have the same instruments during the task, namely two large needle drivers. The 7th degree of freedom corresponds to the opening of the instrument grasper. We also assume for simplification that the left (resp. right) master manipulator controls the left (resp. right) PSM, even though more general tele-operation configurations are possible using the da Vinci robot (Guthart00). During tele-operation, the instruments and the pod are observed by a stereo endoscopic camera, which can be moved using a specific 6 DOF manipulator.

Figure 8:
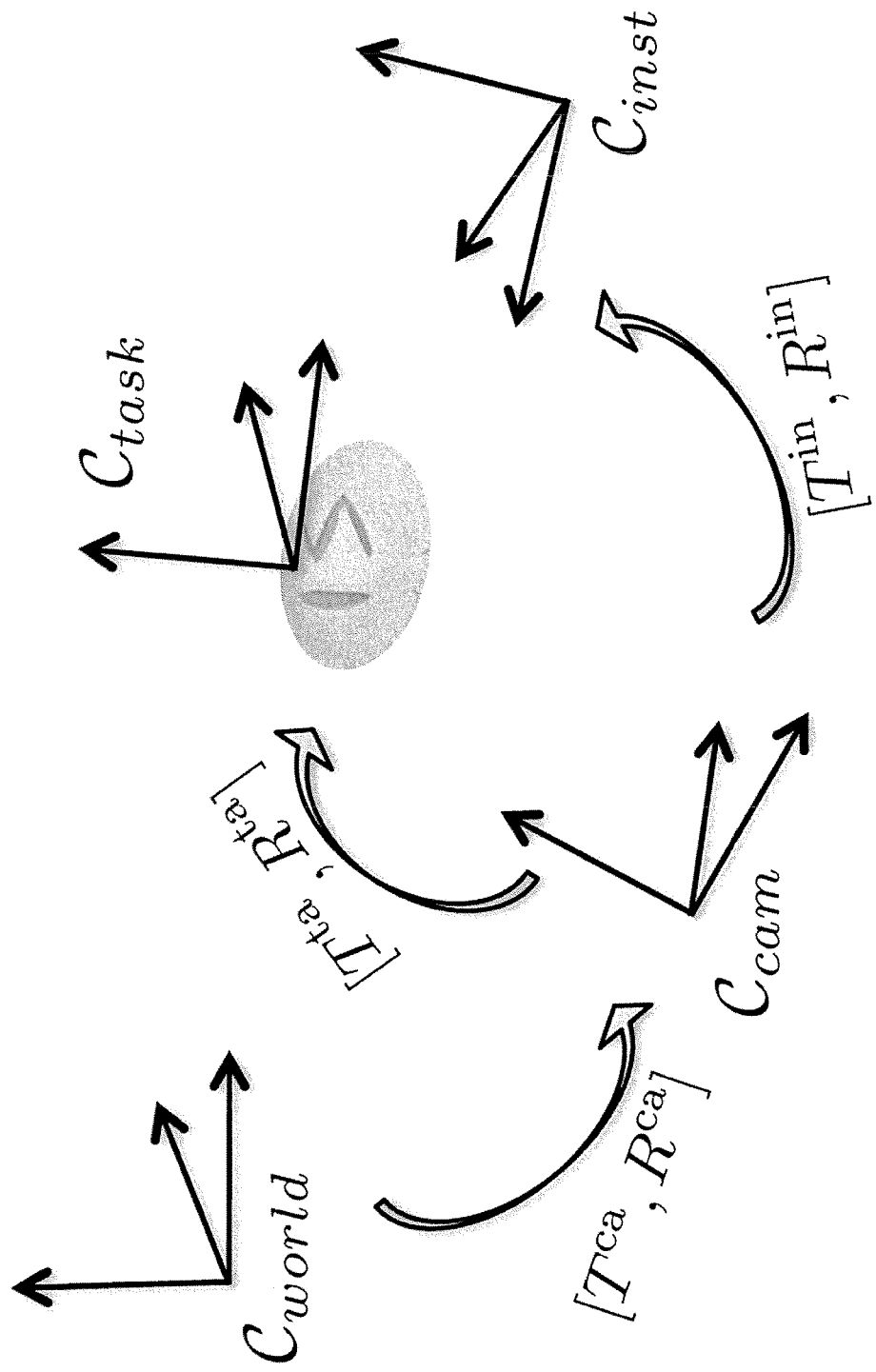
FIG. 8 shows the coordinate systems used in an example according to an embodiment of the current invention.

Four main coordinate systems (or frames) are of importance in this setup (see FIG. 8). The task coordinate system $C_{task}$ is specific to the task and independent of the robot initial kinematics. The camera coordinate system $C_{cam}$ indicates the position of the stereo endoscopic camera and the instrument coordinate systems $C_{inst}^j$ indicates the position of instrument j, with $j \in \{0,1\}$ denoting the left or right instrument. Finally, the origin of the world, for instance representing the base of the robot, is denoted by $C_{world}$.

We denote by $[T,R] \in R^3 \times SO^3$ 3D transformations composed of a translation T and a rotation R. In the following, we assume that we know the transformations $[T_t^{inj}, R_t^{inj}]$ from $C_{cam}$ to $C_{inst}^j$ and $[T_t^{ca}, R_t^{ca}]$ from $C_{world}$ to $C_{cam}$ at each time t. They are collected using the da Vinci research interface (S. DiMaio and C. Hasser, "The da vinci research interface," Insight Journal. [Online]. Available: http://hdl.handle.net/10380/1464). Additionally, we need the transformation $[T_t^{ta}, R_t^{ta}]$ from $C_{cam}$ to $C_{task}$. We obtain this transformation by placing the training pod at a reference world position before starting the task and by using $[T_t^{ca}, R_t^{ca}]$ to track the camera motion. For such short tasks, we assume the pod to remain at its initial reference position. For longer tasks, where the pod could get displaced, the corresponding transformation could be provided by visual pod tracking. We also collect the linear/angular velocities of the two patient side manipulators in Cartesian space, the state of the graspers and for workspace analysis the Cartesian positions of the two master manipulators. We collect these data at a frequency of 40 Hz.

Finally, the stereo endoscopic camera has been calibrated. This permits us to overlay 3D augmented reality information such as trajectories within the stereo view of the surgeon.

Demonstration Data

An operator is asked to demonstrate each task M times, yielding a series of M recordings of the task $\{r^k\}_{1 \leq k \leq M}$. Each recording corresponds to a multi-dimensional time-series $r^k = \{r_1^k, \ldots, r_{|r^k|}^k\}$ of length $|r^k|$ taking its values $r_t^k = (r_t^k, \dot{r}_t^k)$ in $R^{26} = R^{14} \times R^{12}$ for $1 \leq t \leq |r^k|$. The projection $\hat{r}_t^k$ contains the six-dimensional Cartesian velocities as well as the gripper state for the two instruments. These data will be used by the recognition system. The projection $\dot{r}_t^k$ contains the six-dimensional Cartesian positions of the two instruments that will be used for learning control trajectories. Positions are expressed in the task coordinate system to be independent of the robot initial kinematics.

For each $r^k$, the parts of the task that should be automated are labeled by the operator. This decomposes $r^k$ into N data segments $\{r^{(k,1)}, r^{(k,2)}, \ldots, r^{(k,N)}\}$ corresponding to the sub-tasks $\mathcal{T}_1, \ldots, \mathcal{T}_N$. The next sections explain how

- to train a recognition model $H^i$ determining the completion of manual subtask $\mathcal{T}_{2i+1}$, $1 \leq i \leq n$. To do so, we use an HMM built from the training data $\{\hat{r}^{(k,2i+1)}, \hat{r}^{(k,2i+2)}\}_{1 \leq k \leq M}$.
- to compute a trajectory for subtask $\mathcal{T}_{2i}$, $1 \leq i \leq n$, that will be automatically executed by the instrument. To do so, we use a temporal curve averaging technique based on DTW, applied on the data $\{r^{(k,2i)}\}_{1 \leq k \leq M}$.

Recognition

The objective of the recognition system is to determine the completion of each manual task and to perform a seamless transition to automatic control. The operator should naturally perform a continuous motion as if he would start and perform the next subtask manually, until automation takes over the control of the trajectory. To trigger a seamless transition, we need to determine the instant when the operator has reached a point where the automatic trajectory can be initiated. This is done by using a real-time measure of the subtask completion, computed from a temporal model based on HMMs.

A Hidden Markov Model is defined formally as a quintuplet $\lambda = (S, A, O, B, \pi)$ where S is the number of states $x \in \{1, \ldots, S\}$ in the model, A the transition probability matrix between the states, modeling the topology, and O the space of observations, in our case $R^{14}$. B is the observation model, indicating for any observation $o \in O$ and state x the probability $B_x(o) = P(o|x)$ that o can be observed by x. $\pi$ is a probability distribution over the initial states.

To measure the subtask completion, we use an HMM $H^i$ that is constructed from the concatenation of two HMMs $H_0^i$ and $H_1^i$ modeling respectively the manual subtask $\mathcal{T}_{2i+1}$ and the subtask to be automated $\mathcal{T}_{2i+2}$. $H_0^i$ and $H_1^i$ are built respectively from the data $\{\hat{r}^{(k,2i+1)}\}_{1 \leq k \leq M}$ and $\{\hat{r}^{(k,2i+2)}\}_{1 \leq k \leq M}$. For our experiments, we use left-right HMMs and mixture of Gaussians as observation distributions. We initialize the parameters as in (N. Padoy, D. Mateus, D. Weinland, M.-O. Berger, and N. Navab, "Workflow monitoring based on 3d motion features," in Proceedings of the International Conference on Computer Vision Workshops, IEEE Workshop on Video-oriented Object and Event Classification, 2009): the number of states is determined from the length of the training sequences and the probabilities are initialized from the data by splitting the data evenly in as many sequences as available states. Then, expectation-maximization is applied to refine the parameters. When the two HMMs are concatenated, the last state of $H_0^i$ is modified to have a transition to the first state of $H_1^i$. The transition probability is chosen so that the expected time in $H_0^i$ equals the mean duration of the subtask, computed from the training data.

For each state x of HMM $H^i$, we define the binary indicator function $$\gamma(x) = \begin{cases} 0 & \text{if } x \in H_0^i \\ 1 & \text{if } x \in H_1^i \end{cases} \tag{1}$$

We define the probability $\Theta_t$ of having completed the manual subtask at time t by the probability of having reached a state of the HMM that corresponds to the task to be automated:

$$\Theta_t = \sum_{x=1}^{S} \gamma(x) P(X_t = x \mid o_{1:t}) \tag{2}$$

Here, $o_{1:t}$ indicate the observations up to current time t and $X_t$ is a random variable denoting the HMM state at time t. This expression is computed using the forward probabilities of the HMM (L. R. Rabiner, "A tutorial on hidden markov models and selected applications in speech recognition," Proceedings of the IEEE, vol. 77, no. 2, pp. 257-286, 1989).

Finally, the decision of task completion is given by averaging over a short temporal interval δ, using a decision threshold β (0<β<1):

$$\text{completion} \Leftrightarrow \frac{1}{\delta} \sum_{i=t-\delta}^{t} \Theta_i > \beta \tag{3}$$

Automation

Control

The robotic arms are controlled using the da Vinci research interface (DiMaio2008). For each instrument, we use a control mode that superimposes a Cartesian motion $\Delta = [\Delta T \mid \Delta R]$ to the motion caused by the surgeon's manipulation of the master manipulator. In our case, the motion $\Delta$ is given in the camera coordinate system $C_{cam}$.

Let $\{[T_t \mid R_t]\}_{1 \le t \le \tau}$ be a learned trajectory, expressed in the task coordinate system $C_{task}$ and computed as explained in the next section. This trajectory has been normalized by subtracting its initial position, so that $T_1 = 0, R_1 = \text{Id}$. For a given instrument, we execute this relative trajectory at the position of the tool tip at the instant when the automatic execution is started, which we denote by $T_1^{in}$ expressed in $C_{task}$. Our experiments have shown such execution to be a natural way to create a seamless transition between the manual control and the automatic execution. The fact that the trajectory is executed relative to the current tool position when automatic control is initiated leaves the flexibility to the operator to vary his/her manipulation from the exact demonstrated task, e.g. by inserting the needle at different positions.

The superimposed motion is then given for $1 \le t \le \tau$ by $$\begin{cases} \Delta T_t = R_t^{ta} \cdot (T_t + T_1^{in}) + T_t^{ta} \\ \Delta R_t = R_t^{ta} \cdot R_t \cdot R_1^{in} \end{cases} \tag{4}$$

Average Motion Computation

We explain in this section how we learn, for a given instrument, the motion $\{[T_t \mid R_t]\}_{1 \le t \le \tau}$ to be provided to the robot. For an automatic subtask $\mathcal{T}_{2i}$, the motion is computed from the data $\{r^{(k,2i)}\}_{1 \le k \le M}$, in which we only use the Cartesian positions and orientations of the considered instrument. In the following, the rotations are represented by quaternions and we denote this seven-dimensional position data by $\{r^k\}_{1 \le k \le M}$, dropping the index 2i.

We learn a meaningful motion from the demonstrated sequences by using a temporal curve averaging method that has been first presented in (K. Wang and T. Gasser, "Alignment of curves by dynamic time warping," Annals of Statistics, vol. 25, no. 3, pp. 1251-1276, 1997) and then applied successfully on continuous data and also on binary data (S.-A. Ahmadi, T. Sielhorst, R. Stauder, M. Horn, H. Feussner, and N. Navab, "Recovery of surgical workflow without explicit models," in International Conference on Medical Image Computing and Computer-Assisted Intervention (MICCAI), 2006, pp. 420-428). The method consists of an iterative procedure similar to an expectation minimization algorithm, in which all trajectories are temporally synchronized to a reference average trajectory using dynamic time warping (H. Sakoe and S. Chiba, "Dynamic programming algorithm optimization for spoken word recognition," IEEE Trans. Acoust. Speech Signal Process., vol. 26, no. 1, pp. 43-49, 1978) before being averaged. The resulting average is used as reference within the next iteration. Using this approach, the average has a length r equal to the mean length of the input trajectories. Average trajectories generated by this approach can be seen in FIG. 9.

We briefly summarize the approach below:
Let $\tilde{r}^{ref}$ be a reference sequence. Temporally warp $\tilde{r}^k$ to $\tilde{r}^{ref}$ using DTW and denote the warping function by $h^k(t)$.
Compute the average timeline with respect to $\tilde{r}^{ref}$ as $$h(t) = \frac{1}{M} \sum_{k=1}^{M} h^k(t) \tag{5}$$

Compute so-called shift functions $u^k(t) = h^k(h^{-1}(t))$ that permits to transform $\tilde{r}^k$ to the average timeline.
Compute the average $$\tilde{r}^{avg} = \frac{1}{M} \sum_{k=1}^{M} r^k(u^k(t)) \tag{6}$$

Replace $\tilde{r}^{ref}$ by $\tilde{r}^{avg}$ and iterate until convergence.

As initial reference, we recursively merge the input sequences two-by-two, using the same method. We adapted the approach to the motion data in the following way: first, we only use 3D position data for the time-warping synchronization, as position is the dominant feature and we notice that the orientation information does not play a major role for the synchronization in our case. Second, some of the steps above require either interpolating between two quaternions or averaging multiple quaternions. We use respectively SLERP interpolation (E. B. Dam, M. Koch, and M. Lillhohn, "Quaternions, interpolation and animation," University of Copenhagen, Tech. Rep. DIKU-TR98/5, 1998) and spherical averaging (F. L. Markley, Y. Cheng, J. L. Crassidis, and Y. Oshman, "Averaging quaternions," Journal of Guidance, Control, and Dynamics, vol. 30, no. 4, pp. 1193-1196, 2007). After having computed the averaged trajectory in the task coordinate system, we normalize it by subtracting its initial position.

Figure 9B:
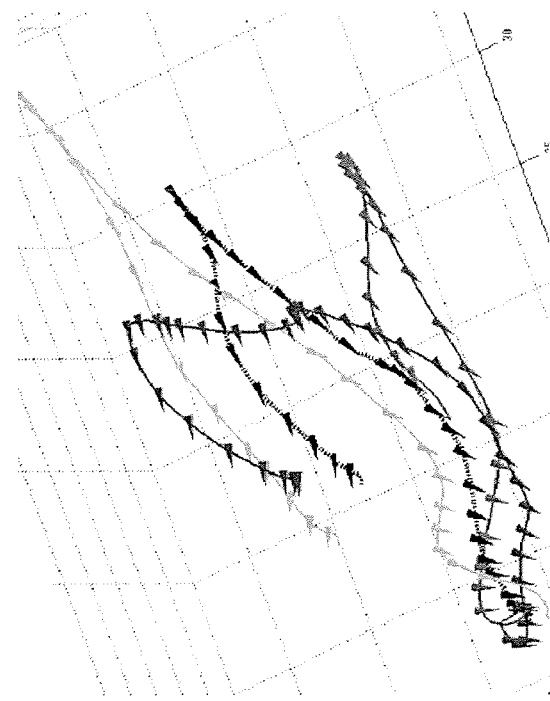
FIGS. 9(a)-9(b) show examples of average trajectories.
Figure 9A:
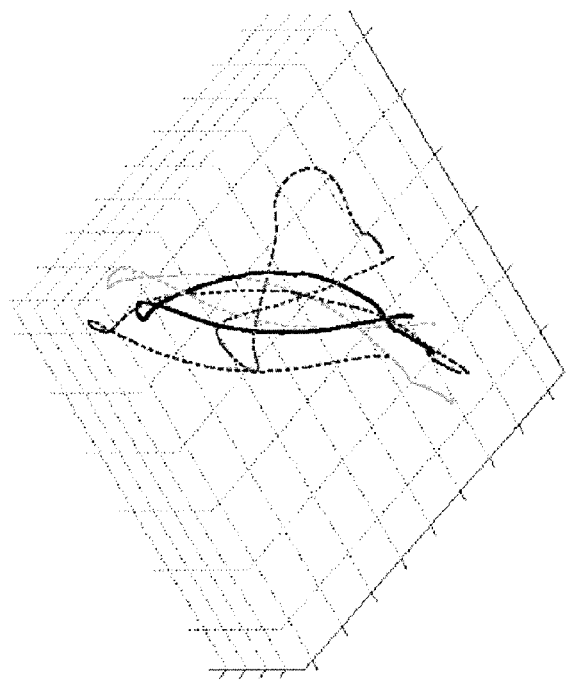

It has been noticed in the literature that if the data are high dimensional or contains multiple local variations, the DTW synchronization can be incorrect. More advanced temporal synchronization techniques like (F. Zhou and F. De la Torre, "Canonical time warping for alignment of human behavior," in Advances in Neural Information Processing Systems Conference (NIPS), December 2009) have been proposed for such cases and can alternatively be used. This is however not the case with our data. We show in FIG. 9(a) how the approach provides a smooth averaged motion from several demonstrated sequences. FIG. 9(b) highlights the rotational motion of a learned trajectory.

Experiments

We have implemented this HMC approach in a modular application based on the CISST libraries (A. Deguet, R. Kumar, R. Taylor, and P. Kazanzides, "The CISST libraries for computer assisted intervention systems," Insight Journal. [Online]. Available: http://hdl.handle.net/10380/1465a), using a da Vinci robot. The application contains five interacting threads with roles: 1) completion recognition, 2) path planning, 3) robot control, 4) visual overlay and 5) main task control.

Figure 11:
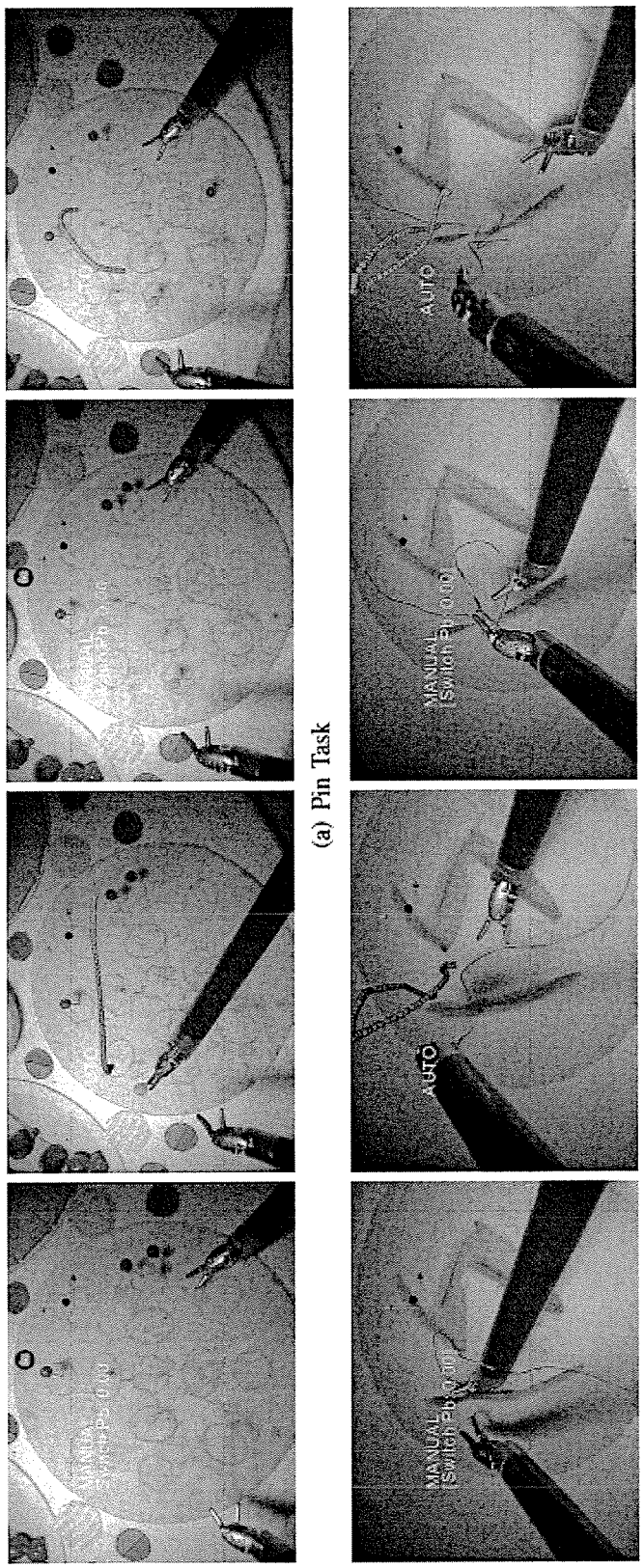
FIG. 11 is an illustration of the tasks performed with the HMC framework. A complete performance can be seen in the illustrative video.

For the experiments, we have performed each task five times to build the task models. Illustrative video shows the view of an operator using our Human-Machine Collaborative system while performing the two illustrative tasks. Within this view, the label "manual" is displayed when the operator is performing the motion. The computed probability of the operator having completed the subtask is also provided. When the control switches to automatic motions, the label "auto" is displayed, as well as the planned trajectory. The displayed trajectory does not exactly overlay with the real position, so as not to interfere with the view of the operator. It is translated to the top of the view instead. This serves the purposes of supervision and cognitive workload reduction of the operator. The video shows seamless transitions between manual operation and automatic execution. It also shows that the da Vinci robot can be operated freely, e.g. by rotating its endoscopic camera. Robustness of the approach to outliers, such as repetitive unsuccessful trials to insert the needle or unexpected closing/opening of the gripper, are illustrated too. We display in FIG. 11 several images taken during the performance of the tasks with the HMC system.

Additional operators have been asked to use the system and have found the transitions seamless and intuitive. It can however happen during the first trial that an operator who has never performed the specific task beforehand does not exactly perform the expected motion. In that case, the completion may be recognized with a short delay, resulting in a trajectory that is slightly translated from the correct and expected position. This requires an adjustment of the tool position in the end. This shows that either a few trials may be necessary for the user to learn how to perform the task correctly (in a way that is similar to the demonstrated data), or that the task models should be built by including data demonstrated by the current operator and illustrating his/her style. In our experiments, the HMMs models use a mixture of two Gaussians and we trigger automatic execution using $\beta=0.9$. We average $\Theta_t$ over 1 second.

Benefits of the approach for easing tele-operation control can include the fact that the motions of the master-manipulators are greatly reduced. Indeed, the large transportation motions are executed automatically and do not require any operator movements. This has two consequences: the need for clutching to readjust the master manipulators becomes almost non-existent and master-manipulator collisions are less likely to occur.

Figure 10A:
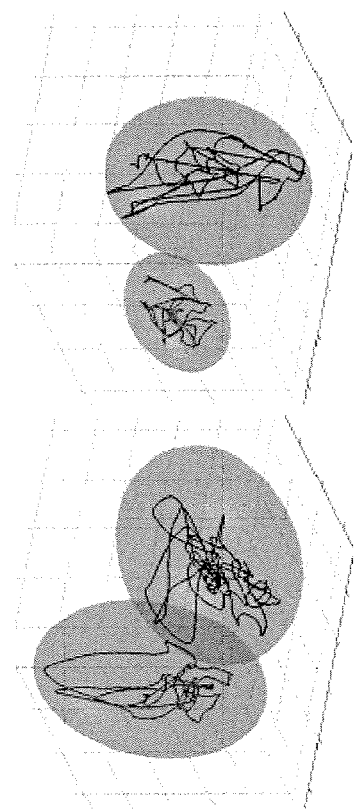
FIGS. 10(a)-10(b) shows workspace analysis of the master manipulators.
Figure 10B:
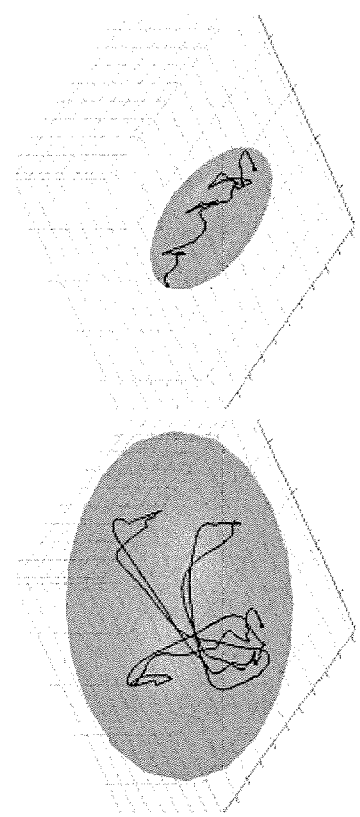

An analysis of the master manipulators workspace is shown in FIG. 10. It compares the master manipulators motions when the HMC system is used or not. For the pin task, FIG. 10(a) shows that the master manipulator workspace is reduced to a much smaller volume when the HMC system is used, since the movement to be accomplished is now restrained to only grasping or pinning down a pin. For the suturing task, only the left instrument is automated. FIG. 10(b) shows that the right manipulator uses a similar workspace when the HMC system is used. The left manipulator, however, uses a much smaller workspace with the HMC framework, as its role is reduced to two fine motions, namely grasping and handing in the needle. The compared standard deviations of the master manipulator positions, in each direction and averaged over 5 sequences, are given in Table 3.

We observe a similar result for the distances traveled by the manipulators: the traveled distance is in average reduced by a factor of 4 during our experiments with the pin task, and by a factor of 1.3 for the suture task. The times for the task completion are similar with and without the use of the HMC approach: in average 48 seconds for the pin task and 64 seconds for the suturing task. It would be straightforward to reduce the times by accelerating the automatic transportation motions.

TABLE 3

Standard deviations of the master manipulator positions (in millimeters), for pin-task (right master manipulator) and sut-task (left master manipulator). Comparison with and without the use of the HMC system.

| | Pin Task | | | Sut Task | | |
|---|---|---|---|---|---|---|
| | x | y | z | x | y | z |
| Manual | 55.4 | 50.4 | 22.1 | 17.7 | 21.4 | 38.3 |
| HMC | 10.6 | 19.9 | 23.1 | 12.1 | 16.7 | 23.2 |

DISCUSSION AND CONCLUSION

In this example, we have described a novel human-machine collaborative approach for tele-surgery based on learning from demonstration according to an embodiment of the current invention. Fine motions are performed by the operator, while real-time recognition of their termination triggers the automatic execution of previously learned motions that do not involve any interaction with the environment. We have shown, using the da Vinci tele-surgical robot, that when such motions are large transportation motions, this form of collaboration improves the usage the master-manipulators workspace. Moreover, experiments show that such human-machine collaboration permits seamless and intuitive switching between manual operation and automatic execution.

Our approach neither requires a complete description of the environment nor motion-preprograming: the recognition system, the executed motion and the ordering of the subtasks are directly inferred from demonstrated sequences in which the automated parts are labeled. Furthermore, by displaying the planned 3D trajectory in the field of view of the operator, he/she can supervise the automated motions. Since the executed motion is superimposed onto the master-manipulator movements, he/she can adjust the trajectory if needed. Finally, the automatic execution can be safely stopped either by clutching the robot or by asking an assistant to stop the control.

This approach can be extended to fine manipulation subtasks, such as needle insertion by taking advantage of visual information provided by the stereo endoscope. Cues from the environment can be incorporated in the learning framework, such as contacts between tissues and instruments, for example. Also longer tasks in which the succession of the subtasks may not be sequential, but could contain options, can also be included.

Finally, in addition to learnt task-specific motions, enhancements to the HMC system can include the capability to automate simple generic motion, for instance triggered by voice command. Generic motions, like the automatic displacement of the camera to focus on a specific tool, could also improve the ergonomic usage of a tele-operated robot.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A semi-automatic, interactive robotic system for performing a multi-step task, comprising:
   a user interface system;
   a recognition system adapted to communicate with said user interface system;
   a control system adapted to communicate with said recognition system; and
   a sensor-actuator system of a robot adapted to communicate with said control system,
   wherein said recognition system is configured to recognize, based on a task model of said multi-step task, actions taken by a user while said user operates said user interface system and instruct said control system to cause said sensor-actuator system of said robot to perform a direct step of said multi-step task,
   wherein said recognition system is further configured to recognize the completion of said direct step, and
   wherein said recognition system is further configured to instruct said control system to cause said sensor-actuator system of said robot to perform an automatic step of said multi-step task upon completion of the direct step based on said recognized actions and said task model of said multi-step task.

2. A semi-automatic, interactive robotic system according to claim 1, wherein said sensor-actuator system of said robot comprises a plurality of articulated arms.

3. A semi-automatic, interactive robotic system according to claim 2, wherein at least one of said plurality of articulated arms comprises at least one of a gripper or a tool attachment assembly.

4. A semi-automatic, interactive robotic system according to claim 1, wherein said task model is a Hidden Markov Model.

5. A semi-automatic, interactive robotic system according to claim 1, wherein said task model is a machine-learning model.

6. A semi-automatic, interactive robotic system according to claim 1, wherein said user interface system comprises a user observation system constructed and arranged to detect and determine motion of at least one portion of said user to communicate with said recognition system to at least one of initiate or modify instructions to be provided to said control system.

7. A semi-automatic, interactive robotic system according to claim 6, wherein said observation system comprises cameras.

8. A semi-automatic, interactive robotic system according to claim 1, wherein said sensor-actuator system of said robot comprises a sensor system constructed and arranged to detect and determine a property of at least one portion of an object being manipulated and to communicate with said recognition system to at least one of initiate or modify instructions to be provided to said control system.

9. A semi-automatic, interactive robotic system according to claim 1, wherein said user interface system comprises an input device adapted to permit said user to at least one of manually or verbally input commands to be communicated to said recognition system to at least one of initiate or modify instructions to be provided to said control system.

10. A semi-automatic, interactive robotic system according to claim 1, wherein said user interface system comprises a display system configured to display information to said user concerning a step to be performed.

11. A semi-automatic, interactive robotic simulation system for simulating a multi-step task, comprising:
    a user interface system;
    a recognition system adapted to communicate with said user interface system;
    a control system adapted to communicate with said recognition system; and
    a simulated sensor-actuator system of a robot adapted to communicate with said control system,
    wherein said recognition system is configured to recognize, based on a task model of said multi-step task, actions taken by a user while said user operates said user interface system and instruct said control system to cause said simulated sensor-actuator system of said robot to simulate the performance of a direct step of said multi-step task,
    wherein said recognition system is further configured to recognize the completion of said direct step, and
    wherein said recognition system is further configured to instruct said control system to cause said sensor-actuator system of said robot to perform an automatic step of said multi-step task upon completion of the direct step based on said recognized actions and said task model of said multi-step task.

12. A semi-automatic, interactive robotic simulation system according to claim 11, wherein said simulated sensor-actuator system of said robot simulates a plurality of articulated arms.

13. A semi-automatic, interactive robotic simulation system according to claim 11, wherein said task model is a Hidden Markov Model.

14. A semi-automatic, interactive robotic simulation system according to claim 11, wherein said task model is a machine-learning model.

15. A semi-automatic, interactive robotic simulation system according to claim 11, wherein said user interface system comprises a display system configured to display information to said user concerning a step to be simulated.

16. A semi-automatic, interactive robotic system according to claim 1, wherein said recognition system is further configured to recognize, upon completion of said automatic step and based on said task model, actions taken by a user while said user operates said user interface system and instruct said control system to cause said sensor-actuator system of said robot to perform a second direct step.

17. A semi-automatic, interactive robotic system according to claim 1, wherein the semi-automatic, interactive robotic system performs a direct step by responding to manual input from said user.

18. A semi-automatic, interactive robotic system according to claim 1, wherein the semi-automatic, interactive robotic system performs an automatic step under the control of the semi-automatic, interactive robotic system, and does not require movements from said user.

* * * * *